United States Patent
Lobdell

(10) Patent No.: US 6,743,245 B2
(45) Date of Patent: Jun. 1, 2004

(54) ASYNCHRONOUS METHOD OF OPERATING MICROSURGICAL INSTRUMENTS

(75) Inventor: Donn D. Lobdell, Corona Del Mar, CA (US)

(73) Assignee: Alcon Universal Ltd., Hunenberg (CH)

( * ) Notice: Subject to any disclaimer, the term of this patent is extended or adjusted under 35 U.S.C. 154(b) by 331 days.

(21) Appl. No.: 09/738,242

(22) Filed: Dec. 15, 2000

(65) Prior Publication Data

US 2001/0031976 A1 Oct. 18, 2001

Related U.S. Application Data

(60) Provisional application No. 60/172,690, filed on Dec. 20, 1999.

(51) Int. Cl.[7] .......................... A61B 17/32; A61B 17/20
(52) U.S. Cl. .......................... 606/171; 604/22; 604/28; 604/31; 604/35; 606/170; 600/565
(58) Field of Search .......................... 606/171, 170, 606/168, 180, 167, 174; 604/19, 22, 27, 28, 30, 31, 35; 600/564, 565, 566, 567

(56) References Cited

U.S. PATENT DOCUMENTS

| 3,884,238 A | 5/1975 | O'Malley et al. ............ 128/305 |
| 4,577,629 A | 3/1986 | Martinez ..................... 128/305 |
| 4,696,298 A | 9/1987 | Higgins et al. ............. 128/305 |
| 4,757,814 A | 7/1988 | Wang et al. ................. 128/318 |
| 4,819,635 A | 4/1989 | Shapiro ....................... 128/305 |
| 4,909,249 A | 3/1990 | Akkas et al. ................. 606/107 |
| 4,909,782 A * | 3/1990 | Semm et al. ................. 606/171 |
| 4,940,468 A | 7/1990 | Petillo ........................ 606/170 |
| 4,986,827 A | 1/1991 | Akkas et al. ................. 606/107 |
| 5,019,035 A | 5/1991 | Missirlian et al. ............ 604/22 |
| 5,024,652 A | 6/1991 | Dumenek et al. .............. 604/22 |
| 5,047,008 A | 9/1991 | de Juan, Jr. et al. .......... 604/22 |
| 5,059,204 A | 10/1991 | Lawson et al. .............. 606/171 |
| 5,061,238 A | 10/1991 | Shuler .......................... 604/22 |
| 5,176,628 A | 1/1993 | Charles et al. ................ 604/22 |
| 5,284,472 A | 2/1994 | Sussman et al. .............. 604/22 |
| 5,354,268 A | 10/1994 | Peterson et al. .............. 604/35 |
| 5,380,280 A | 1/1995 | Peterson ...................... 604/65 |
| 5,423,844 A | 6/1995 | Miller ........................ 606/171 |
| 5,429,136 A * | 7/1995 | Milo et al. .................. 600/439 |
| 5,474,532 A | 12/1995 | Steppe ......................... 604/22 |
| 5,520,652 A | 5/1996 | Peterson ..................... 604/119 |
| 5,630,827 A | 5/1997 | Vijfvinkel ................... 606/171 |
| 5,674,194 A | 10/1997 | Jung et al. .................... 604/65 |
| 5,685,840 A * | 11/1997 | Schechter et al. ............ 604/22 |
| 5,733,297 A | 3/1998 | Wang ......................... 606/167 |
| 5,782,849 A | 7/1998 | Miller ........................ 606/159 |
| 5,833,643 A | 11/1998 | Ross et al. ................... 604/22 |
| 5,928,218 A * | 7/1999 | Gelbfish ..................... 604/540 |
| 6,010,496 A | 1/2000 | Appelbaum et al. ........... 606/4 |
| 6,102,926 A * | 8/2000 | Tartaglia et al. ............ 606/170 |
| 6,258,111 B1 * | 7/2001 | Ross et al. .................. 606/171 |
| 6,572,578 B1 * | 6/2003 | Blanchard ..................... 604/22 |
| 2003/0078609 A1 * | 4/2003 | Finlay et al. ................ 606/171 |

* cited by examiner

Primary Examiner—Henry Bennett
Assistant Examiner—Kathryn Odland
(74) Attorney, Agent, or Firm—W. David Lee

(57) ABSTRACT

An improved, asynchronous method of operating a microsurgical instrument, such as a vitrectomy probe. The instrument includes a port for receiving tissue and an inner cutting member. A flow of tissue is induced into the port with a vacuum source. The port is at least partially occluded with the tissue. The occlusion is detected, and the inner cutting member is actuated to close the port and cut the tissue.

16 Claims, 3 Drawing Sheets

ASYNCHRONOUS METHOD OF OPERATING MICROSURGICAL INSTRUMENTS

This application claims the priority of U.S. Provisional Application No. 60/172,690, filed Dec. 20, 1999.

FIELD OF THE INVENTION

The present invention generally pertains to a method of operating microsurgical instruments. More particularly, but not by way of limitation, the present invention pertains to a method of operating microsurgical instruments used in posterior segment ophthalmic surgery, such as vitrectomy probes.

DESCRIPTION OF THE RELATED ART

Many microsurgical procedures require precision cutting and/or removal of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibers that are often attached to the retina. Therefore, cutting and removal of the vitreous must be done with great care to avoid traction on the retina, the separation of the retina from the choroid, a retinal tear, or, in the worst case, cutting and removal of the retina itself.

The use of microsurgical cutting probes in posterior segment ophthalmic surgery is well known. Such vitrectomy probes are typically inserted via an incision in the sclera near the pars plana. The surgeon may also insert other microsurgical instruments such as a fiber optic illuminator, an infusion cannula, or an aspiration probe during the posterior segment surgery. The surgeon performs the procedure while viewing the eye under a microscope.

Conventional vitrectomy probes typically include a hollow outer cutting member, a hollow inner cutting member arranged coaxially with and movably disposed within the hollow outer cutting member, and a port extending radially through the outer cutting member near the distal end thereof. Vitreous humor is aspirated into the open port, and the inner member is actuated, closing the port. Upon the closing of the port, cutting surfaces on both the inner and outer cutting members cooperate to cut the vitreous, and the cut vitreous is then aspirated away through the inner cutting member. U.S. Pat. Nos. 4,577,629 (Martinez); 5,019,035 (Missirlian et al.); 4,909,249 (Akkas et al.); 5,176,628 (Charles et al.); 5,047,008 (de Juan et al.); 4,696,298 (Higgins et al.); and 5,733,297 (Wang) all disclose various types of vitrectomy probes, and each of these patents is incorporated herein in its entirety by reference.

Conventional vitrectomy probes include "guillotine style" probes and rotational probes. A guillotine style probe has an inner cutting member that reciprocates along its longitudinal axis. A rotational probe has an inner cutting member that reciprocates around its longitudinal axis. In both types of probes, the inner cutting members are actuated using various methods. For example, the inner cutting member can be moved from the open port position to the closed port position by pneumatic pressure against a piston or diaphragm assembly that overcomes a mechanical spring. Upon removal of the pneumatic pressure, the spring returns the inner cutting member from the closed port position to the open port position. As another example, the inner cutting member can be moved from the open port position to the closed port position using a first source of pneumatic pressure, and then can be moved from the closed port position to the open port position using a second source of pneumatic pressure. As a further example, the inner cutting member can be electromechanically actuated between the open and closed port positions using a conventional rotating electric motor or a solenoid. U.S. Pat. No. 4,577,629 provides an example of a guillotine style, pneumatic piston/mechanical spring actuated probe. U.S. Pat. Nos. 4,909,249 and 5,019,035 disclose guillotine style, pneumatic diaphragm/mechanical spring actuated probes. U.S. Pat. No. 5,176,628 shows a rotational dual pneumatic drive probe.

With each of the above-described conventional vitrectomy probes, the inner cutting member is always actuated, and thus the port is opened and closed, at a particular cycle or cut rate. When the port is open, it is most often occluded by pieces of vitreous humor or other tissue that are being aspirated into the open port via vacuum. Such tissue is not cut and aspirated away from the port until the next stroke of the inner cutting member as determined by the given cut rate. Therefore, conventional vitrectomy probes spend more time in an occluded state than actually cutting and aspirating away tissue. In addition, when actuation of the inner cutting member is determined by a given cut rate, there is sometimes no vitreous or other tissue located in the port to cut when the inner member is actuated.

Given the above, a need exists for an improved method of operating a vitrectomy probe or other microsurgical cutting instrument that does not suffer from the above-described limitations. The improved method should be safe for the patient, easy for the surgeon to use, and economically feasible.

SUMMARY OF THE INVENTION

One aspect of the present invention comprises a method of operating a microsurgical instrument. The instrument includes a port for receiving tissue and an inner cutting member. A flow of tissue is induced into the port with a vacuum source. The port is at least partially occluded with the tissue. The occlusion is detected, and the inner cutting member is actuated to close the port and cut the tissue.

The microsurgical instrument may comprise a vitrectomy probe or other cutting probe. The occlusion may be detected by detecting a decrease in fluid flow in the inner cutting member, or a portion of the instrument or a surgical system fluidly coupled to the inner cutting member. The occlusion may also be detected by detecting an increase in vacuum in the inner cutting member, or a portion of the instrument or a surgical system fluidly coupled to the inner cutting member.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1 through 7 of the drawings, like numerals being used for like and corresponding parts of the various drawings.

Figure 1:
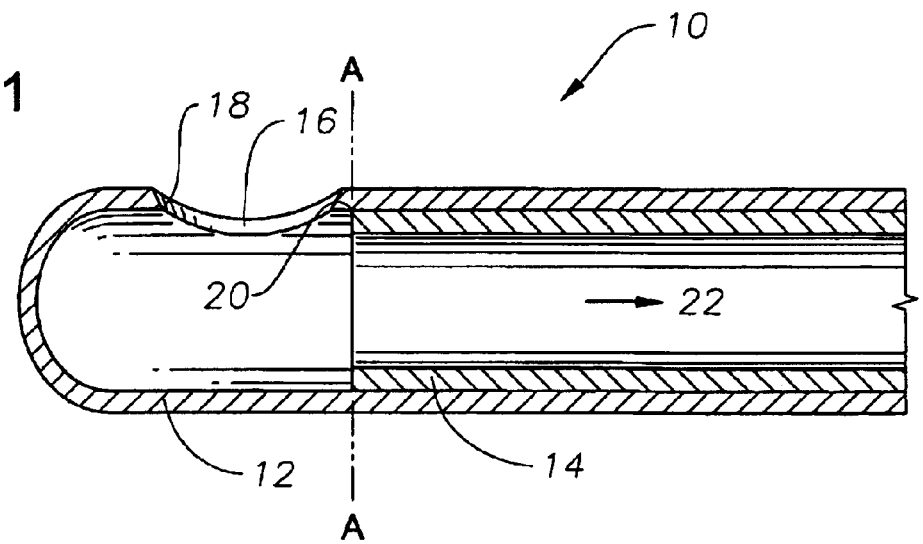
FIG. 1 is a side sectional view of a first vitrectomy probe preferred for use in the method of the present invention shown in the fully open port position.
Figure 2:
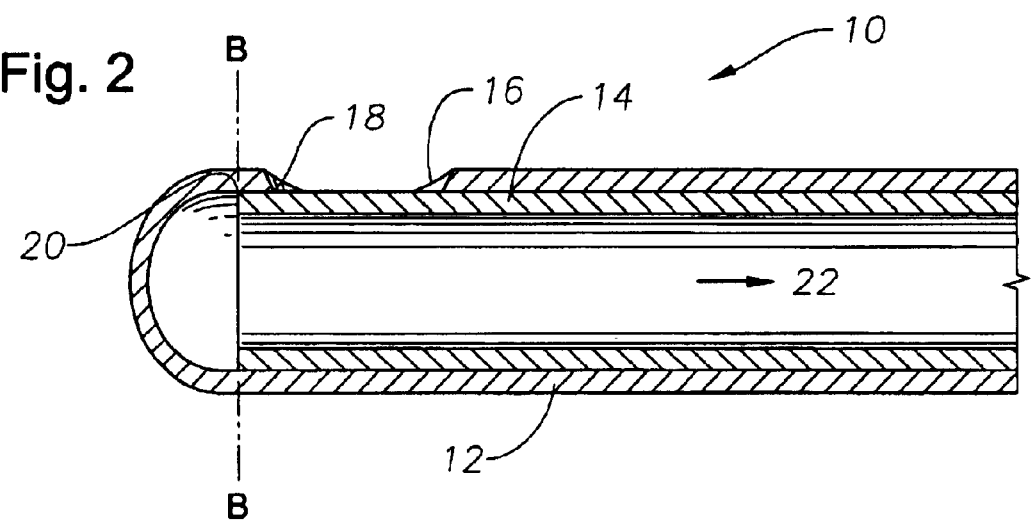
FIG. 2 is a side sectional view of the probe of FIG. 1 shown in a closed port position.

Referring first to FIGS. 1 and 2, a distal end of a microsurgical instrument 10 is schematically illustrated. Microsurgical instrument 10 is preferably a guillotine style vitrectomy probe and includes a tubular outer cutting member 12 and a tubular inner cutting member 14 movably disposed within outer cutting member 12. Outer cutting member 12 has a port 16 and a cutting edge 18. Port 16 preferably has a length of about 0.020 inches along the longitudinal axis of probe 10. Inner cutting member 14 has a cutting edge 20.

During operation of probe 10, inner cutting member 14 is moved along the longitudinal axis of probe 10 from a position A as shown in FIG. 1, to a position B as shown in FIG. 2, and then back to position A in a single cut cycle. Position A corresponds to a fully open position of port 16, and position B corresponds to a fully closed position of port 16. In position A, vitreous humor or other tissue is aspirated into port 16 and within inner cutting member 14 by vacuum induced fluid flow represented by arrow 22. In position B, the vitreous within port 16 and inner cutting member 14 is cut or severed by cutting edges 18 and 20 and is aspirated away by vacuum induced fluid flow 22. Cutting edges 18 and 20 are preferably formed in an interference fit to insure cutting of the vitreous. In addition, positions A and B are conventionally located somewhat outside the ends of port 16 to account for variations in the actuation of inner cutting member 14 in specific probes 10.

Figure 3:
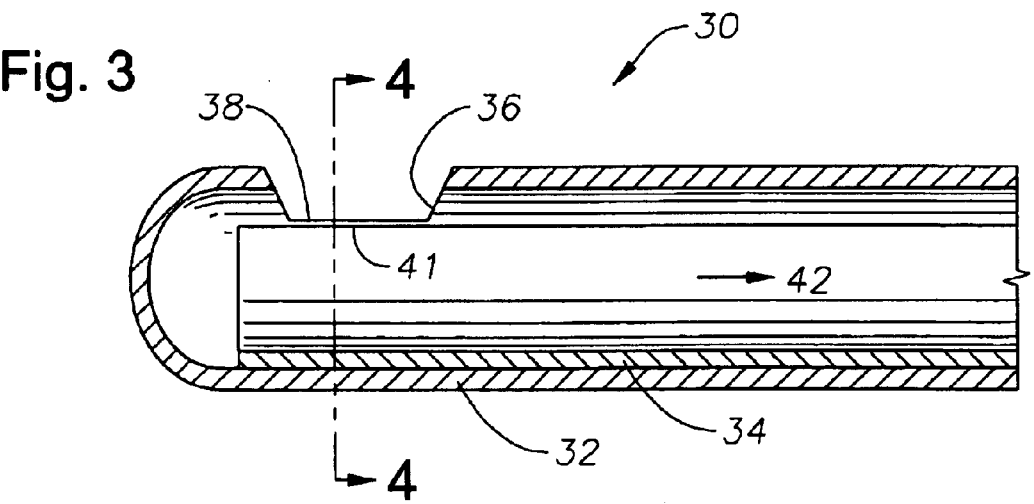
FIG. 3 is a side, partially sectional view of a second vitrectomy probe preferred for use in the method of the present invention shown in a fully open port position.
Figures 4, 5:
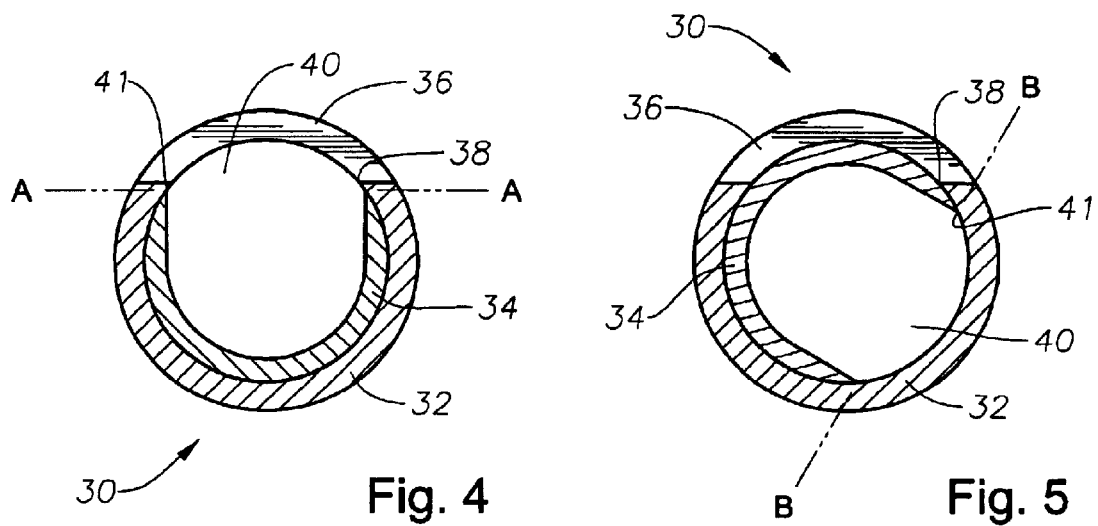
FIG. 4 is a cross-sectional view of the probe of FIG. 3 along line 4—4.
FIG. 5 is a cross-sectional view of the probe of FIG. 3 along line 4—4 shown in a closed port position.

Referring now to FIGS. 3 through 5, a distal end of a microsurgical instrument 30 is schematically illustrated. Instrument 30 is preferably a rotational vitrectomy probe and includes a tubular outer cutting member 32 and a tubular inner cutting member 34 movably disposed within outer cutting member 32. Outer cutting member 32 has a port 36 and a cutting edge 38. Port 36 preferably has a length of about 0.020 inches along the longitudinal axis of probe 30. Inner cutting member 34 has an opening 40 having a cutting edge 41.

During operation of probe 30, inner cutting member 34 is rotated about the longitudinal axis of probe 30 from a position A as shown in FIG. 4, to a position B as shown in FIG. 5, and then back to position A in a single cut cycle. Position A corresponds to a fully open position of port 36, and position B corresponds to a fully closed position of port 36. In position A, vitreous humor or other tissue is aspirated into port 36, opening 40, and inner cutting member 34 by vacuum induced fluid flow represented by arrow 42. In position B, the vitreous within inner cutting member 34 is cut or severed by cutting edges 38 and 41 and is aspirated away by vacuum induced flow 42. Cutting edges 38 and 41 are preferably formed in an interference fit to insure cutting of the vitreous. In addition, position B is conventionally located somewhat past the edge of cutting surface 38 of outer cutting member 32 to account for variations in the actuation of inner cutting member 34 in specific probes 30.

Inner cutting member 14 of probe 10 is preferably moved from the open port position to the closed port position by application of pneumatic pressure against a piston or diaphragm assembly that overcomes a mechanical spring. Upon removal of the pneumatic pressure, the spring returns inner cutting member 14 from the closed port position to the open port position. Inner cutting member 34 of probe 20 is preferably moved from the open port position to the closed port position using a first source of pneumatic pressure, and then moved from the closed port position to the open port position using a second source of pneumatic pressure. The first source of pneumatic pressure is pulsed, and the second source of pneumatic pressure may be pulsed or fixed. Alternatively, inner cutting members 14 and 34 can be electromechanically actuated between their respective open and closed port positions using a conventional linear motor or solenoid. The implementation of certain ones of these actuation methods is more fully described in U.S. Pat. Nos. 4,577,629; 4,909,249; 5,019,035; and 5,176,628 mentioned above. For purposes of illustration and not by way of limitation, the method of the present invention will be described hereinafter with reference to a guillotine style, pneumatic/mechanical spring actuated vitrectomy probe 10.

Figure 6:
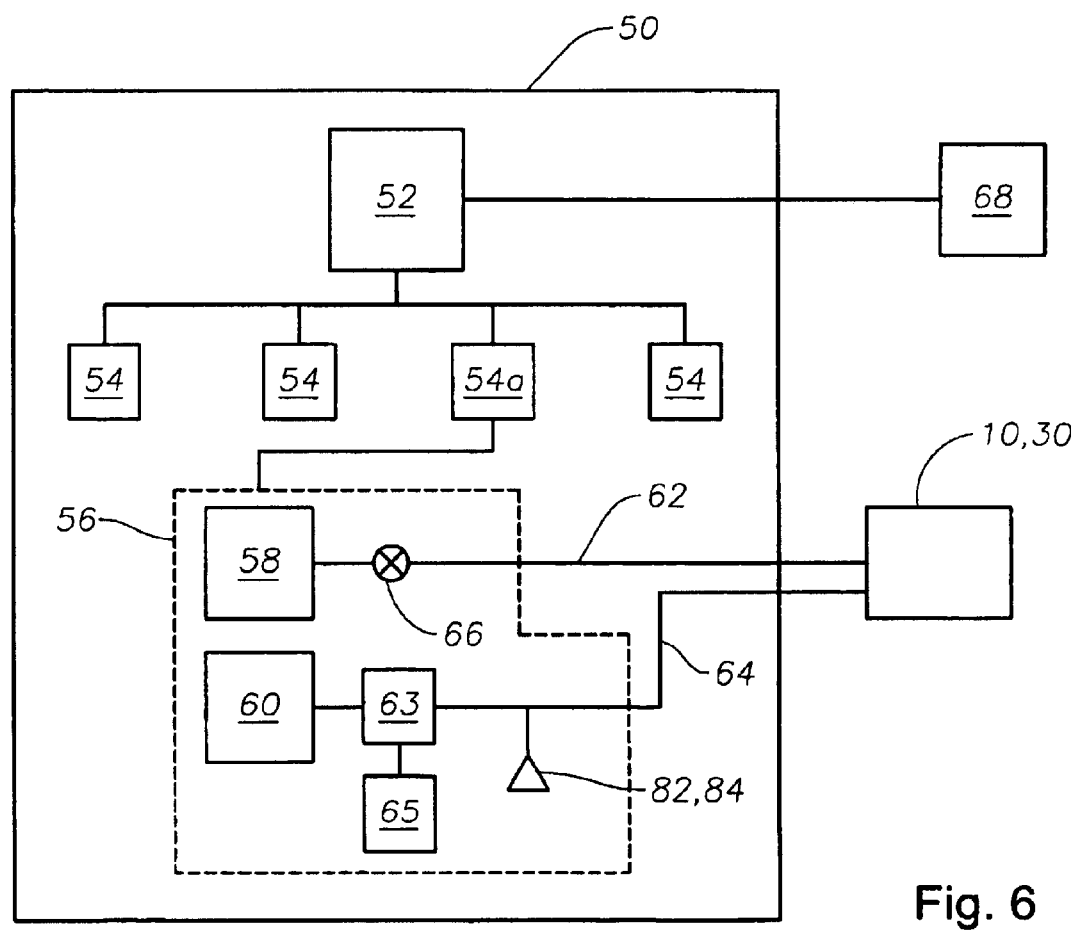
FIG. 6 is a block diagram of certain portions of a microsurgical system preferred for use in the method of the present invention.

FIG. 6 shows a block diagram of certain portions of the electronic and pneumatic sub-assemblies of a microsurgical system 50 preferred for use in the present invention. For example, system 50 could be the Accurus® surgical system available from Alcon Laboratories, Inc. of Fort Worth, Tex. or another conventional ophthalmic microsurgical system. System 50 preferably includes a host microcomputer 52 that is electronically connected to a plurality of microcontrollers 54. Microcomputer 52 preferably comprises an Intel® 486™ microprocessor, and microcontrollers 54 preferably comprise Intel® 80C196™ microprocessors. Of course, other conventional microprocessors having equivalent or superior performance can be utilized for microcomputer 52 and microcontrollers 54, if desired. Microcontroller 54a is electronically connected with and controls an air/fluid module 56 of system 50. Air/fluid module 56 preferably includes a source of pneumatic pressure 58 and a source of vacuum 60, both of which are in fluid communication with probe 10 or probe 30 via conventional PVC tubing 62 and 64. Vacuum source 60 preferably comprises a venturi coupled to a pneumatic pressure source. Alternatively, vacuum source 60 may include a positive displacement pump, such as a peristaltic, diaphragm, centrifugal, or scroll pump, or another conventional source of vacuum. A surgical cassette 63 is preferably disposed between aspiration line 64 and vacuum source 60. A collection bag 65 is preferably fluidly coupled to cassette 63 for the collection of aspirated tissue and other fluid from the eye. Air/fluid module 56 also preferably includes appropriate electrical connections between its various components. Although both probes 10 and 30 may be used with system 50, the remainder of this description of system 50 will only reference probe 10 for ease of description.

Pneumatic pressure source 58 provides pneumatic drive pressure to probe 10, preferably at a pressure of about 57 psi. A solenoid valve 66 is disposed within tubing 62 between pneumatic pressure source 58 and probe 10. Solenoid valve 66 preferably has a response time of about 2 to about 3 milliseconds. System 50 also preferably includes a variable controller 68. In a conventional mode of operation of probe 10, variable controller 68 is preferably electronically connected with and controls solenoid valve 66 via microcomputer 52 and microcontroller 54a. In this mode of operation, variable controller 68 provides a variable electric signal that cycles solenoid valve 66 between open and closed positions so as to provide a cycled pneumatic pressure that drives inner cutting member 14 of probe 10 from its open port position to its closed port position at a variety of cut rates. Although not shown in FIG. 6, air/fluid module 56 may also include a second pneumatic pressure source and solenoid valve controlled by microcontroller 54a that drives inner cutting member 34 of probe 30 from its closed port position to its open port position. Variable controller 68 is preferably a conventional foot switch or foot pedal that is operable by a surgeon. For example, variable controller 68 may be the foot pedal sold as part of the Accurus® surgical system mentioned above. Alternatively, variable controller 68 could also be a conventional hand held switch or "touch screen" control, if desired.

Figure 7:
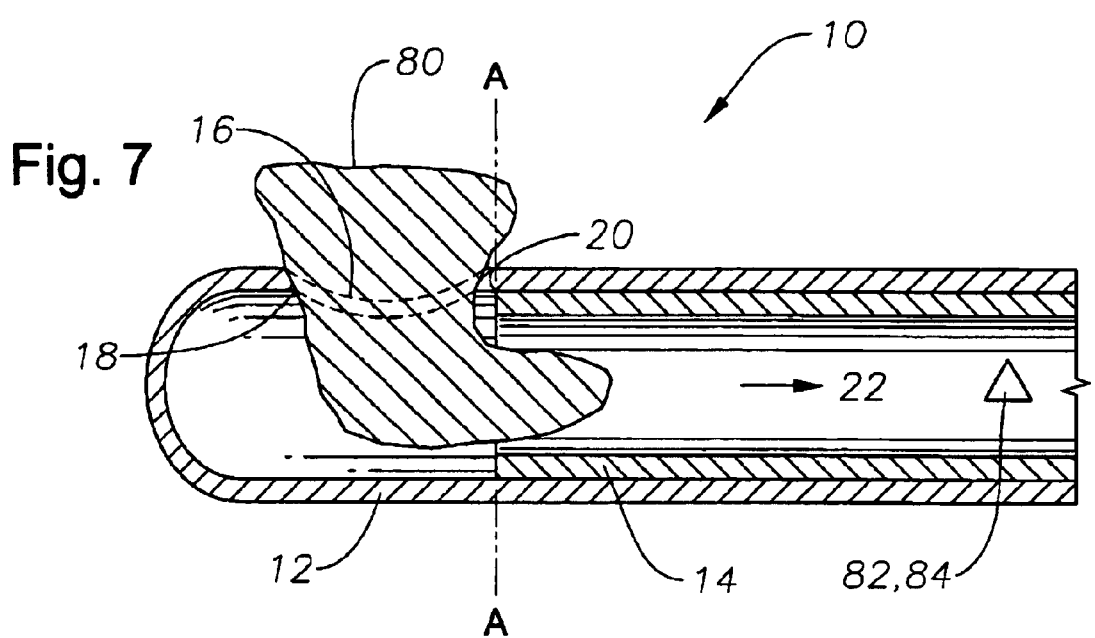
FIG. 7 is a side sectional view of the probe of FIG. 1 with its port occluded by tissue.

The preferred method of operating probe 10 according to the present invention will now be described in greater detail in connection with FIGS. 1, 2, 6, and 7. As shown in FIG. 1, port 16 is in the fully open position A and vitreous humor or other tissue is aspirated into port 16 and within inner cutting member 14 by vacuum induced fluid flow 22 created by vacuum source 60. Referring to FIG. 7, a piece of tissue 80, for example a piece of vitreous humor, traction band, or membrane, occludes port 16 due to this vacuum. Tissue 80 will not be cut, and the cut portion of tissue 80 will not be aspirated away by vacuum induced fluid flow 22, until inner cutting member 14 is actuated to its fully closed position B, as shown in FIG. 2.

In the conventional operation of probe 10, this cutting occurs in a periodic manner as determined by the given cycle or cut rate of inner cutting member 14. However, according to the present invention, inner cutting member 14 is actuated from position A to position B in an asynchronous manner whenever it is determined that port 16 is occluded. An occlusion of port 16 may be identified by detecting the decrease in fluid flow in inner cutting member 14, or a portion of probe 10 or surgical system 50 fluidly coupled to inner cutting member 14, that occurs when port 16 is fully or partially occluded. An occlusion of port 16 may also be identified by detecting the increase in vacuum that occurs in inner cutting member 14, or a portion of probe 10 or surgical system 50 fluidly coupled to inner cutting member 14, that occurs when port 16 is fully or partially occluded. A flow meter 82, pressure transducer 84, or other conventional sensors may be used to detect this change in flow or vacuum. As shown schematically in FIG. 7, sensors 82 and/or 84 are located in a portion of probe 10 in fluid communication with inner cutting member 14. Alternatively, as shown schematically in FIG. 6, sensors 82 and/or 84 are located within surgical system 50 and are fluidly coupled to inner cutting member 14 via aspiration line 64.

Sensors 82 and/or 84 are preferably electronically connected to microcontroller 54a. When a change in flow or vacuum is sensed, this information, or an appropriate electrical signal, is passed to microcontroller 54a. Microcontroller 54a sends a pulsed electrical signal that opens solenoid valve 66 for a given time period. Upon the opening of solenoid valve 66, pneumatic pressure source 58 provides pneumatic pressure that drives inner cutting member 14 from a fully open port position A to a fully closed port position B, cutting tissue 80. Upon the closing of solenoid valve 66, inner cutting member 14 returns to fully open port position A. This cycle repeats itself whenever another piece of tissue 80 occludes port 16.

Although the preferred method of asynchronous operation of a microsurgical instrument has been described above with reference to a pneumatic/mechanical spring actuated probe 10, it will be apparent to one skilled in the art that it is equally applicable to a dual pneumatically actuated probe 30. In addition, the preferred method is also applicable to vitrectomy probes that are actuated using a conventional linear electrical motor, solenoid, or other electromechanical apparatus.

From the above, it may be appreciated that the present invention provides an improved method of operating a vitrectomy probe or other microsurgical cutting instrument. The improved method is more efficient in the cutting and aspirating of tissue than conventional methods. The improved method is safe for the patient, easy for the surgeon to use, and economically feasible.

The present invention is illustrated herein by example, and various modifications may be made by a person of ordinary skill in the art. For example, although identifying an occlusion of the port of the microsurgical instrument is described above in terms of detecting a change in fluid flow or vacuum within the instrument, other conventional sensing apparatus may be used to detect such an occlusion.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of operating a microsurgical instrument, said instrument comprising a port for receiving tissue and an inner cutting member, comprising the steps of:

inducing a flow of tissue into said port with a vaccum source;

at least partially occluding said port with said tissue;

detecting said occlusion of said port using a flow sensor; and actuating said inner cutting member to close said port and cut said tissue in response to said detecting step.

2. The method of claim 1 wherein said actuating step comprises reciprocating said inner cutting member along a longitudinal axis of said instrument.

3. The method of claim 1 wherein said actuating step comprises reciprocating said inner cutting member around a longitudinal axis of said instrument.

4. The method of claim 1 wherein said microsurgical instrument is a vitrectomy probe.

5. The method of claim 1 wherein said detecting step comprises detecting a decrease in fluid flow in said inner cutting member.

6. The method of claim 1 wherein said detecting step comprises detecting a decrease in fluid flow in a portion of said instrument fluidly coupled to said inner cutting member.

7. The method of claim 1 wherein said detecting step comprises detecting a decrease in fluid flow in a portion of a surgical system fluidly coupled to said inner cutting member.

8. The method of claim 1 wherein said occluding step comprises fully occluding said port with said tissue.

9. A method of operating a microsurgical instrument, said instrument comprising a port for receiving tissue and an inner cutting member, comprising the steps of:

inducing a flow of tissue into said port with a vacuum source;

at least partially occluding said port with said tissue;

detecting said occlusion of said port using a pressure sensor; and actuating said inner cutting member to close said port and cut said tissue in response to said detecting step.

10. The method of claim 1 wherein said actuating step comprises reciprocating said inner cutting member along a longitudinal axis of said instrument.

11. The method of claim 1 wherein said actuating step comprises reciprocating said inner cutting member around a longitudinal axis of said instrument.

12. The method of claim 1 wherein said microsurgical instrument is a vitrectomy probe.

13. The method of claim 1 wherein said detecting step comprises detecting an increase in vacuum in said inner cutting member.

14. The method of claim 1 wherein said detecting step comprises detecting an increase in vacuum in a portion of said instrument fluidly coupled to said inner cutting member.

15. The method of claim 1 wherein said detecting step comprises detecting an increase in vacuum in a portion of a surgical system fluidly coupled to said inner cutting member.

16. The method of claim 1 wherein said occluding step comprises fully occluding said port with said tissue.

* * * * *